US012773331B2

(12) United States Patent
Northrop et al.

(10) Patent No.: US 12,773,331 B2
(45) Date of Patent: Oct. 27, 2026

(54) IMPLANT DELIVERY ASSEMBLY WITH DISTAL PROTECTION

(71) Applicants: STRYKER CORPORATION, Kalamazoo, MI (US); STRYKER EUROPEAN OPERATIONS LIMITED, Carrigtwohill (IE)

(72) Inventors: Clay W. Northrop, Salt Lake City, UT (US); Aleksandr Leynov, Walnut Creek, CA (US); Siddharth Loganathan, Santa Clara, CA (US); Danny Lai, Kalamazoo, MI (US); Jonathan Gibbs, Kalamazoo, MI (US); Samit Mustafa, Kalamazoo, MI (US)

(73) Assignees: Stryker Corporation, Kalamazoo, MI (US); Stryker European Operations Limited, Carrigtwohill (IE)

( * ) Notice: Subject to any disclaimer, the term of this patent is extended or adjusted under 35 U.S.C. 154(b) by 346 days.

(21) Appl. No.: 18/661,573

(22) Filed: May 11, 2024

(65) Prior Publication Data

US 2024/0293243 A1 Sep. 5, 2024

Related U.S. Application Data

(63) Continuation of application No. PCT/US2022/078940, filed on Oct. 28, 2022.

(Continued)

(51) Int. Cl.
*A61F 2/95* (2013.01)
*A61F 2/966* (2013.01)

(52) U.S. Cl.
CPC .............. *A61F 2/95* (2013.01); *A61F 2/9661* (2020.05); *A61F 2002/9511* (2013.01)

(58) Field of Classification Search
CPC ...... A61F 2/013; A61F 2/95; A61F 2230/005; A61F 2/014; A61F 2/962; A61F 2/9522
See application file for complete search history.

(56) References Cited

U.S. PATENT DOCUMENTS 11,344,400 B2 * 5/2022 Yeh ........................ A61F 2/013
2009/0028729 A1 1/2009 Jochumsen et al.

(Continued)

OTHER PUBLICATIONS

PCT International Search Report and Written Opinion dated Feb. 2, 2023 for International App No. PCT/US2022/078940, Applicant: Stryker Corporation et al., (10 pages).

*Primary Examiner* — Kevin T Truong
(74) *Attorney, Agent, or Firm* — Vista IP Law Group, LLP

(57) ABSTRACT

A delivery system for deploying a medical implant includes a delivery wire assembly disposed within a delivery catheter lumen, the assembly having an implant loading region configured for seating the implant when the assembly is constrained within the delivery catheter lumen and the implant is in a compressed configuration, the assembly further including an implant distal protection having a central portion coupled to the assembly, distal of the implant loading region, and a peripheral portion extending proximally from the central portion to at least partially cover a distal end portion of the implant when the assembly, implant and distal protection are constrained within the catheter lumen, wherein the peripheral portion remains extending in the proximal direction when the implant assumes an expanded configuration after being released from the catheter lumen, and the peripheral portion of the distal protection comprises a plurality of stems, each comprising a respective petal-like member.

20 Claims, 10 Drawing Sheets

Related U.S. Application Data

(60) Provisional application No. 63/293,755, filed on Dec. 25, 2021.

(56) References Cited

U.S. PATENT DOCUMENTS

| | | | | |
|---|---|---|---|---|
| 2010/0057184 | A1* | 3/2010 | Randolph | A61F 2/962<br>623/1.36 |
| 2014/0067037 | A1 | 3/2014 | Fargahi | |
| 2014/0172067 | A1* | 6/2014 | Brown | A61B 90/39<br>623/1.12 |
| 2021/0038362 | A1* | 2/2021 | Yeh | A61F 2/013 |

* cited by examiner

IMPLANT DELIVERY ASSEMBLY WITH DISTAL PROTECTION

RELATED APPLICATION DATA

This application is a continuation of International Patent Application No. PCT/US2022/078940, filed on Oct. 28, 2022, which claims priority to U.S. Provisional Patent Application No. 63/293,755, filed on Dec. 25, 2021, the disclosures of all of which are hereby incorporated herein by reference in their entirety into the present application.

FIELD

The presently disclosed inventions relate generally to minimally invasive assemblies used for delivering medical implants. More particularly, the present disclosure relates to delivery assemblies for delivering medical implants, such as a tubular stent or flow diverter, to a targeted implantation site in the vasculature of a patient.

BACKGROUND

The use of intravascular implants, such as stents, stent grafts, flow-diverters, aneurysm occlusive devices, vena cava filters, etc., has become an effective method for treating many types of vascular disease. In general, a suitable intravascular implantable device is inserted into the vascular system of the patient and navigated through the vasculature to a targeted implantation site using a delivery system, such as a catheter having a delivery lumen. Using currently available delivery apparatus, virtually any target site in the patient's vascular system may be accessed, including the coronary, cerebral, and peripheral vasculature.

Minimally invasive delivery devices include catheters that are percutaneously introduced into the patient's vasculature over a guidewire, wherein an open distal end of the catheter is navigated to a targeted implantation site using well-known techniques. A medical implant is then deployed through a delivery lumen of the catheter in a compressed (i.e., reduced diameter) delivery configuration, and then introduced into a lumen of a blood vessel through the distal end opening of the catheter. For example, self-expanding implants, such as stents, are delivered in an elastically compressed state while being confined within the tubular catheter delivery lumen, and then elastically expand once deployed out the open distal end of the catheter and into engagement with the interior wall of the blood vessel. The expanded and enlarged stent supports and reinforces the vessel wall, thereby maintaining the vessel in an open and unobstructed condition.

Medical implants may have a variety of sizes and shapes. For example, stents and some flow-diverters usually assume an expanded, substantially tubular configuration when deployed within the vasculature of a patient. Further, medical implants can be made from a variety of materials, including polymers (e.g., nonbioerodable and bioerodable plastics) and metals. Medical implants can be made from shape memory or superelastic materials, such as shape memory metals (e.g., shape memory Nitinol) and polymers (e.g., polyurethane). Such shape memory implants can be induced (e.g., by temperature, electrical or magnetic field or light) to take on a shape (e.g., a radially expanded shape) after delivery to a treatment site. Superelastic embolic materials, such as superelastic Nitinol, take on a shape after delivery without the need for an inductive stimulus. Other commonly used materials include stainless steel, platinum and elgiloy. Drug delivery implants can carry, and/or the surface of the device, can be coated with bioactive or therapeutic agents. Commonly used medical implants, such as stents, stent grafts, flow-diverters, may be composed of a plurality of filaments (e.g., wires) that are braided or woven into predetermined (e.g., tubular) shape, or may be made out of laser cut tubes.

Known delivery systems may include retainer sleeves to control release or covers to protect the ends of the implants during deployment, which are illustrated and described (by way of example) in U.S. Pat. Nos. 6,478,814, 6,830,575 and 8,591,566. Such sleeves/covers include winged or separate members that may be more challenging to manufacture and may increase resistive or frictional forces imposed by the device assembly when being pushed through the delivery catheter, negatively impacting the overall performance of the delivery system.

Therefore, there is an ongoing need to provide an implant delivery system for delivering self-expanding implants that facilitates protection of the implant, while avoiding or minimizing an increase in resistive or frictional forces through the delivery catheter.

By way of illustration, FIG. 1 depicts an implant delivery system 100, constructed according to the one embodiment of the disclosed inventions. The implant delivery system 100 generally comprises an elongate, tubular delivery catheter 120 having a proximal end portion 130, a distal end portion 160, and a lumen 125 extending there between, wherein the delivery catheter lumen 125 is in communication with respective open proximal and distal ends of the delivery catheter 120. The delivery catheter 120 is coaxially disposed within, and movable relative to, an outer sheath 180 that is used to help position the distal end portion 160 of the delivery catheter 120 within a target portion of the vasculature. The proximal end portion 130 of the delivery catheter 120 includes a fluid port 150 (distal to a proximal opening in the outer sheath 180 through which the delivery catheter 120 is inserted) used to introduce fluids into the lumen 125. The fluid delivery port 150 remains outside of the patient's body so as to be accessible to the physician/operator when the implant delivery system 100 is inserted into a patient's vasculature. The distal portion 160 of the delivery catheter 120 is sized and dimensioned to access remote locations within the vasculature, such as, e.g., within the neurovasculature. And may have a smaller diameter (or profile) than the proximal portion 130.

The implant delivery system 100 further includes an implant delivery wire assembly 300 (described below in greater detail in conjunction with FIGS. 2A-D), including a core wire 350 that is pushed through the delivery catheter lumen 125 for delivering an implant 200 (not shown in FIG. 1) carried on a distal end portion of the core wire 350 to a targeted site in a patient's vasculature. As depicted in FIG. 1, the core wire 350 has been inserted through the proximal end opening of the delivery catheter 120, and pushed through the delivery lumen 125, such that an atraumatic distal tip portion 380 (e.g., a soft coil member) attached to a distal end of the core wire 350 is extending out a distal end opening of the delivery catheter 120.

The outer sheath 180 may be introduced into the vasculature over a guidewire (not shown) that has been previously introduced, known as an over-the-wire configuration), or alternatively may be introduced in a "rapid-exchange" configuration, where a guidewire extends through only a distal portion of the outer sheath 180 from a guidewire port (not shown), as is well-known. The delivery catheter 120 is then introduced through the outer sheath, whether over the guidewire or otherwise, again, as is well-known. The outer sheath 180 includes a radiopaque marker 355 adjacent to an open distal end of the sheath to assist with positioning thereof in a targeted location of the vasculature.

The delivery catheter 120 may be composed of suitable polymeric materials, metals and/or alloys, such as polyethylene, stainless steel or other suitable biocompatible materials or combinations thereof. In some instances, the proximal portion 130 may include a reinforcement layer, such a braided layer or coiled layer to enhance pushability. The delivery catheter 120 may include one or more transition regions between the proximal portion 130 and the distal portion 160. The distal end portion 160 may have an outer diameter less than the outer diameter of the proximal portion 130 in order to reduce the profile of the distal end portion 160, and facilitate navigation of the distal end portion 160 extending out the distal opening of the outer sheath 180 in tortuous vasculature. The proximal end portion 130 may be formed from material that is stiffer than the distal portion 160 of the delivery catheter 120, so that the proximal portion 130 has sufficient pushability to advance through the patient's vascular system, while the distal portion 160 may be formed of a more flexible material so that the distal portion 160 may remain flexible and track more easily over a guidewire to access remote locations in tortuous regions of the vasculature. As best seen in FIG. 2A, a tapered radiopaque marker 455, and atraumatic tip 457, respectively, are disposed proximate a distal end opening 452 of the delivery catheter 120.

By way of further illustration, FIGS. 2A-D depicts the implant 200, which may be a stent, a flow diverter, or other type of vasculature implant, is carried on a distal portion of the core wire 350. The implant 200 may comprise a variety of biocompatible materials, such as stainless steel, elgiloy, nickel, titanium, nitinol, shape memory polymers, or combinations thereof, and may be constructed using well-known techniques, such as by etching or cutting a pattern from a tube or sheet of stent material, or by weaving/braiding one or more wires or ribbons into a desired shape and pattern. The implant 200 may include further components that are welded, bonded or otherwise engaged to one another, and may optionally include a non-porous, non-permeable biocompatible material, cover or the like.

As seen in FIG. 2D, the implant 200 is generally tubular and has a proximal portion 220, a distal portion 240, with an inner lumen 260 extending therebetween. The implant 200 is depicted in FIGS. 2A-D in a compressed, elongated delivery configuration, radially constrained within the lumen 125 of the delivery catheter 120. The implant 200 is preferably biased to self-expand radially outwards into an expanded deployed configuration when deployed out the distal end opening of (i.e., no longer radially constrained within) the delivery catheter 120.

Further illustrating in FIGS. 2A-B, the core wire 350 of the delivery wire assembly 300 is coaxially disposed within the delivery catheter lumen 125, and the implant 200 is coaxially disposed around the core wire 350, also constrained within the delivery catheter lumen 125. In particular, the core wire 350 is axially movable relative to the delivery catheter 120, with the delivery wire assembly 300 being configured to engage the implant 200 as the core wire 350 is axially translated through the delivery catheter lumen 125 for delivery of the implant 200 at a targeted implantation site in a vasculature. The interface between the delivery wire assembly 300 and the implant 200 is described in further detail below.

Radiopaque markers 360 (e.g., laser etched, radiopaque bands or any other suitable markers) are preferably located along the distal portion of the core wire 350 to assist in positioning the core wire 350 and implant 200 relative to the delivery catheter 120. In the illustrated embodiment, a coil 357 is disposed around the core wire 350 for providing structural support just proximal of the implant 200. A radiopaque marker band 360 is disposed on a distal portion 358 of the coil 357 to indicate the location of the proximal end portion 220 of the implant 200. An epoxy bond 376 is used to attach the marker 360 to the core wire 350.

By way of illustration in FIGS. 2B-C, a re-sheathing pad 370 is disposed around the core wire 350 distal of the coil 357, and an implant re-sheathing bumper 375 is attached to the core wire 350 at the distal end of the re-sheathing pad 370. An epoxy bond 376 is used to attach the re-sheathing bumper to the core wire 350. This region of the core wire 350 onto which the implant 200 is loaded is referred to herein as the implant loading region. In particular, the proximal portion 220 of the implant 200 is disposed over the respective re-sheathing pad 370 and re-sheathing bumper 375, and a distal end of the distal portion 240 of the implant 200 is covered by a distal protection feature 500 (FIG. 2A) that is attached to the core wire 350 and secured between respective proximal and distal locking members 550. In FIG. 2A, only the distal locking member 550 is shown, as the proximal locking member 550 is obscured by the implant distal protection feature 500. The atraumatic distal tip 380 (e.g., a soft coil member) is attached to the core wire 350 proximate to the distal locking member 550 (FIG. 2B).

SUMMARY

In one embodiment of the disclosed inventions, a delivery system is provided for deploying an implant at a target site within a mammalian vasculature, the implant having a compressed delivery configuration and an expanded deployed configuration. The delivery system comprises a delivery catheter having a lumen, an elongate delivery wire assembly at least partially disposed within the delivery catheter lumen, the delivery wire assembly being translatable relative to the delivery catheter and having an implant loading region configured for seating the implant when a distal portion of the delivery wire assembly including the implant is constrained within the delivery catheter lumen and the implant is in the compressed delivery configuration. The delivery system further includes an implant distal protection comprising a central portion coupled to the delivery wire assembly distal of the implant loading region, and a peripheral portion extending proximally from the central portion to at least partially cover a distal end portion of the implant when the distal portion of the delivery wire assembly including the implant and implant distal protection is constrained within the delivery catheter lumen. The peripheral portion of the implant distal protection is configured to expand when the peripheral portion of the implant distal protection is no longer constrained by the delivery catheter. Further, the peripheral portion of the implant distal protection is configured to not evert from a proximally facing direction to a distally facing direction so that the peripheral portion of the implant distal protection remains extending in the proximally facing direction when the implant assumes the expanded deployed configuration after the implant has been released from the delivery catheter lumen and is no longer covered by the peripheral portion of the implant distal protection. Additionally, the peripheral portion of the implant distal protection comprises a plurality of circumferentially spaced elongated stems, each comprising a respective petal-like member, where the plurality of stems extend from the central portion.

In various embodiments, respective petal-like members are disposed and/or cover each of the elongated stems of the peripheral portion of the implant distal protection.

In one embodiment, the respective petal-like members, comprises a first petal-like member disposed on or covering between about eighty percent to about ninety percent of a total length of the respective elongated stem, a second petal-like member disposed on or covering between about sixty percent to about fifty percent of the total length of the respective elongated stem, and a third petal-like member disposed on or covering between about forty percent to about thirty percent of the total length of the respective elongated stem.

In some embodiments, the petal-like members are substantially evenly circumferentially spaced around the delivery wire assembly. The petal-like members comprise an arcuate, annular strip, or concave configuration.

In other embodiments, the central portion of the implant distal protection is fixedly attached to the delivery wire assembly in a manner such that the implant distal protection is not rotatable relative to the delivery wire assembly. Alternatively, the central portion of the implant distal protection is attached to the delivery wire assembly in a manner such that the implant distal protection is rotatable relative to the delivery wire assembly.

In some embodiments, the implant distal protection covers about twenty percent of a total length of the implant when the distal portion of the delivery wire assembly including the implant and implant distal protection is constrained within the delivery catheter lumen. In other embodiments, the implant distal protection covers between about ten percent and about twenty percent of a total length of the implant when the distal portion of the delivery wire assembly including the implant and implant distal protection is constrained within the delivery catheter lumen. In yet other embodiments, the implant distal protection covers between about five percent and about ten percent of a total length of the implant when the distal portion of the delivery wire assembly including the implant and implant distal protection is constrained within the delivery catheter lumen. In further embodiments, the implant distal protection covers about five percent or less of a total length of the implant when the distal portion of the delivery wire assembly including the implant and implant distal protection is constrained within the delivery catheter lumen.

Optionally, the implant distal protection is configured to exert negligible or insignificant forces over the distal portion of the implant as the implant expands from the compressed delivery configuration to the expanded deployed configuration.

Optionally, the implant distal protection is configured to expand from the compressed delivery configuration to the expanded deployed configuration in a sequential order, wherein the first petal-like member expands, then, the second petal-like member expands and lastly, the third petal-like member expands.

Optionally, the implant distal protection substantially retains a compressed delivery configuration after the implant distal protection radially expands and is no longer constrained by the delivery catheter.

Optionally, the implant distal protection is configured to not evert to the distally facing direction as the implant expands.

Optionally, the implant distal protection is configured to be withdrawn back into the delivery catheter without everting from the proximally facing direction to the distally facing direction.

Optionally, the implant distal protection comprises a biocompatible material having a thickness of about 0.0006", a length of about 0.0173".

Optionally, the respective petal-like members, comprises a first petal-like member disposed on or covering between about sixty percent to about ninety percent of a total length of the respective elongated stem, and a second petal-like member disposed on or covering between about fifty percent to about thirty percent of the total length of the respective elongated stem. In this embodiment, the implant distal protection is configured to expand from the compressed delivery configuration to the expanded deployed configuration in a sequential order, wherein the first petal-like member expands, then, the second petal-like member expands.

Optionally, the respective petal-like members comprises more than three respective petal-like members, the respective petal-like members disposed on or covering different percentages of the total length of their respective elongated stems. In this embodiment, the implant distal protection is configured to expand from the compressed delivery configuration to the expanded deployed configuration in a sequential order, wherein the plurality of the petal-like member expands one after another petal-like member.

Other and further aspects and features of embodiments of the herein disclosed inventions will become apparent from the ensuing detailed description in view of the accompanying figures.

DETAILED DESCRIPTION

Figure 1:
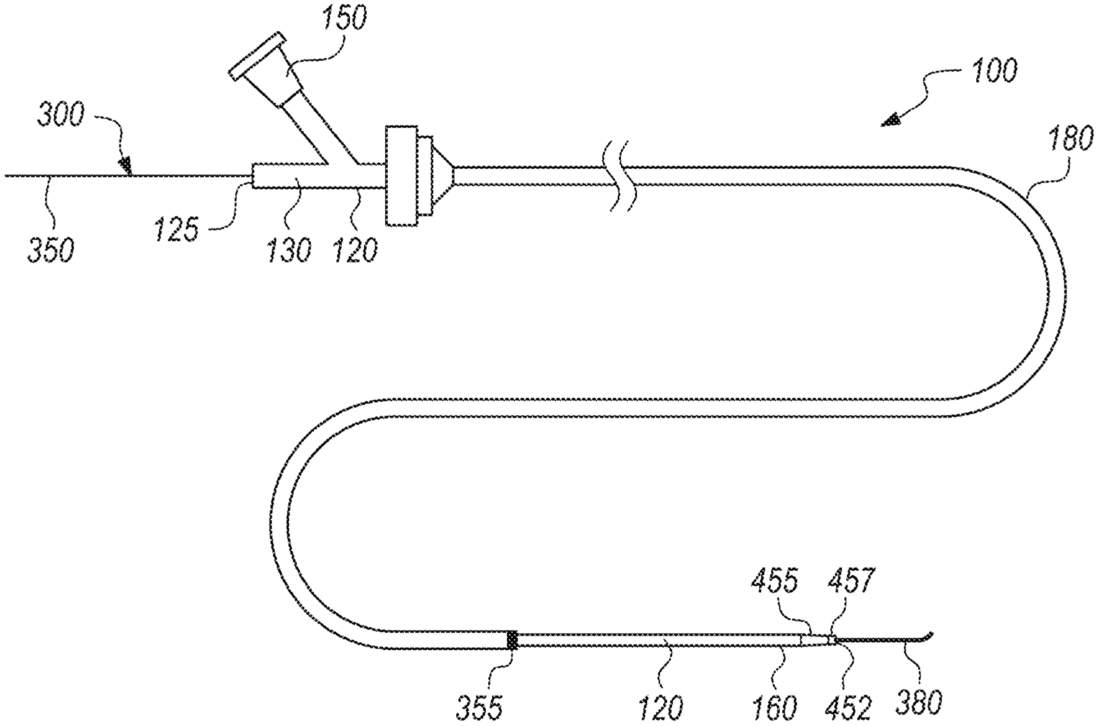
FIG. 1 (Prior Art)
FIG. 1 is a side view of an implant delivery system (Prior Art).
Figure 2A:
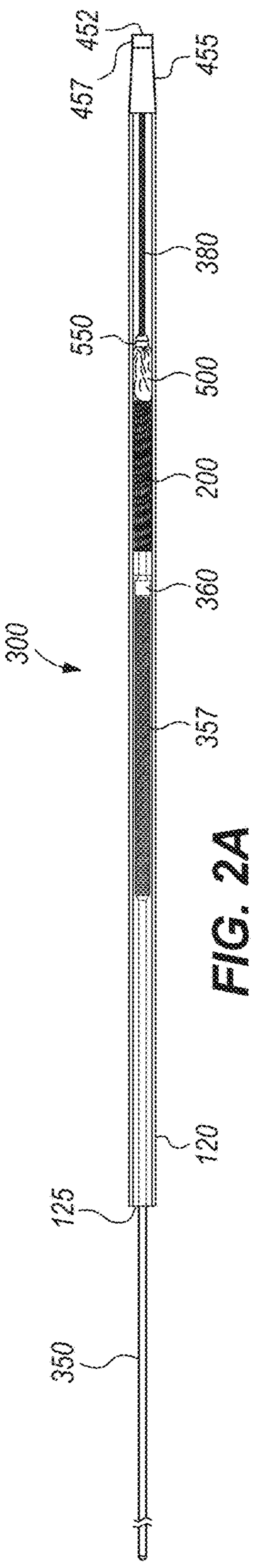
FIG. 2A (Prior Art)
FIGS. 2A-E are partially cut-away side, perspective and exploded views of a delivery wire assembly (Prior Art) of the implant delivery system of FIG. 1, showing portions of the system in greater detail.
Figure 2B:
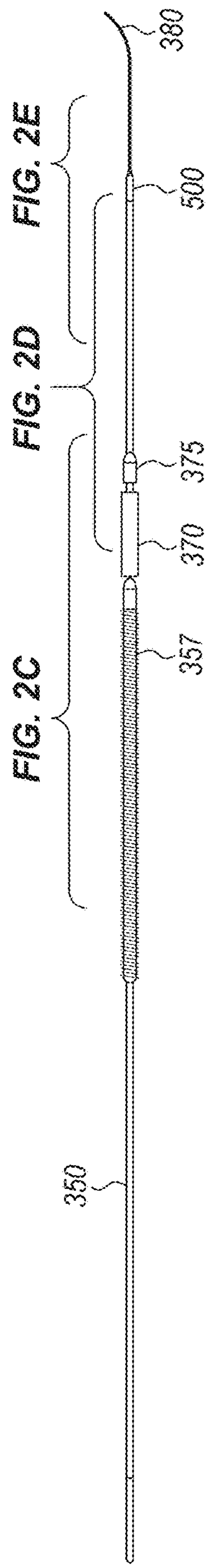
FIG. 2B (Prior Art)
Figure 2D:
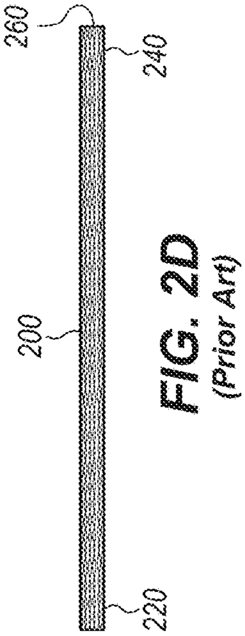
FIG. 2D (Prior Art)
Figure 2E:
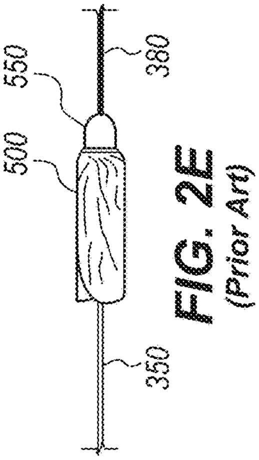
FIG. 2E (Prior Art)
Figure 2C:
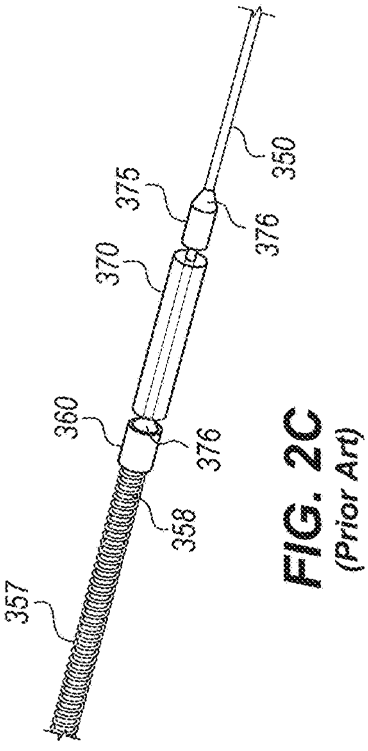
FIG. 2C (Prior Art)

For the following defined terms, these definitions shall be applied, unless a different definition is given in the claims or elsewhere in this specification.

All numeric values are herein assumed to be modified by the terms "substantially" or "about," whether or not explicitly indicated. The terms "substantially" and "about" refer to a range of numbers that one of skill in the art would consider equivalent to the recited parameter, structure or value (i.e., having the same function or result). In many instances, the terms "about" and "substantially" include numbers that are rounded to the nearest significant figure. The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used in this specification and the appended claims, the terms "proximal" and "proximally" (and the like) when used to describe a relative position, the location or direction of a structure or action of the implant delivery system that is towards the outside of the patient's body; and the terms "distal" and "distally" (and the like) when used to describe a relative position, the location or direction of a structure or action of the implant delivery system that is extended deepest into the patient's body.

Various embodiments of the disclosed inventions are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the disclosed inventions, or as a limitation on the scope thereof, which is defined only by the appended claims and their equivalents.

In addition, the respective illustrated embodiments of the disclosed inventions need not have all of the depicted features, and a feature, aspect or advantage described in conjunction with a particular embodiment is not necessarily limited to that embodiment, but can be practiced in other embodiments, even if not so illustrated.

Figure 3A:
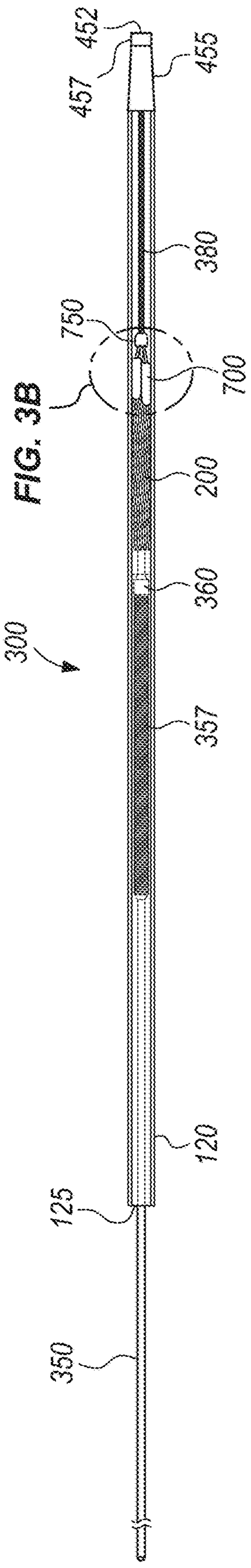
FIGS. 3A-B are partially cut-away side and detailed view of a delivery wire assembly of the implant delivery system, showing the implant distal protection, according to one embodiment of the disclosed inventions.

FIG. 3A illustrates the implant delivery wire assembly 300 of the implant delivery system 100, including an implant distal protection 700, according to one embodiment of the disclosed inventions. The core wire 350 that is pushed through the delivery catheter lumen 125 (FIG. 1) for delivering the implant 200 carried on a distal end portion of the core wire 350 into a targeted site in a patient's vasculature. The implant 200 may be a stent, a flow diverter, or other type of vasculature implant, and may comprise a variety of biocompatible materials, as previously disclosed. The implant 200 is depicted in FIG. 3A in a compressed, elongated delivery configuration disposed (i.e., radially constrained) within the lumen 125 of the delivery catheter 120. The implant 200 is preferably biased to self-expand radially outwards into an expanded deployed configuration when deployed out the distal end opening of (i.e., no longer radially constrained within) the delivery catheter 120. The core wire 350 of the delivery wire assembly 300 is coaxially disposed within the delivery catheter lumen 125, and the implant 200 is coaxially disposed around the core wire 350, also constrained within the delivery catheter lumen 125. Radiopaque markers 360 (e.g., laser etched, radiopaque bands or any other suitable markers) are preferably located along the distal portion of the core wire 350 to assist in positioning the core wire 350 and implant 200 relative to the delivery catheter 120. The coil 357 is disposed around the core wire 350 for providing structural support just proximal of the implant 200. The tapered radiopaque marker 455, and atraumatic tip 457, respectively, are disposed proximate a distal end opening 452 of the delivery catheter 120. In FIG. 3A, a distal locking member 750 is shown, as a proximal locking member 750' is obscured by the implant distal protection 700. In the illustrated embodiment, the implant distal protection 700 is fixedly attached to the core wire 350 by the locking members 750, so that the implant distal protection does not rotate relative to the core wire 350.

In an alternative embodiment, the implant distal protection 700 may be attached to a collar (not shown) that is still fixed in a relative longitudinal position on the core wire 350 by the locking members 750 in a manner that allows the collar, and thus the implant distal protection 700, to rotate relative to the core wire 350 and locking members 750. The rotatable implant distal protection 700 is configured to allow torque transmission to the distal end of the core wire 350 (e.g., atraumatic distal tip portion 380), which further allows vessel selection and facilitates navigation of the delivery wire assembly 300 to the targeted implantation site. When the implant distal protection 700 rotates with respect to the core wire 350, any externally induced (e.g., by patient's anatomy, user, clinician) relative torsion between the delivery catheter 120 and the core wire 350 is avoided or substantially minimized, preventing accumulation of torsional energy, detrimental to the deployment of the implant 200. As such, the rotatable implant distal protection 700 is configured to prevent accumulation of torsional energy in the delivery wire assembly 300 and the implant 200, when assembly 300 and implant 200 are in the delivery configuration (e.g., radially constrained) disposed within the lumen 125 of the delivery catheter 120.

Figure 3B:
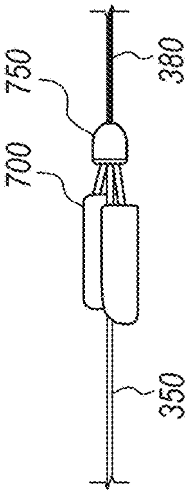

Additionally, the atraumatic distal tip 380 (e.g., a soft coil member) is attached to the core wire proximate to the distal locking member 550 (FIGS. 3A-B). FIG. 3B illustrate a close-up view of the implant distal protection 700 in a compressed, elongated delivery configuration (i.e., radially constrained). The implant distal protection 700 will be described in further detail below.

Figure 4A:
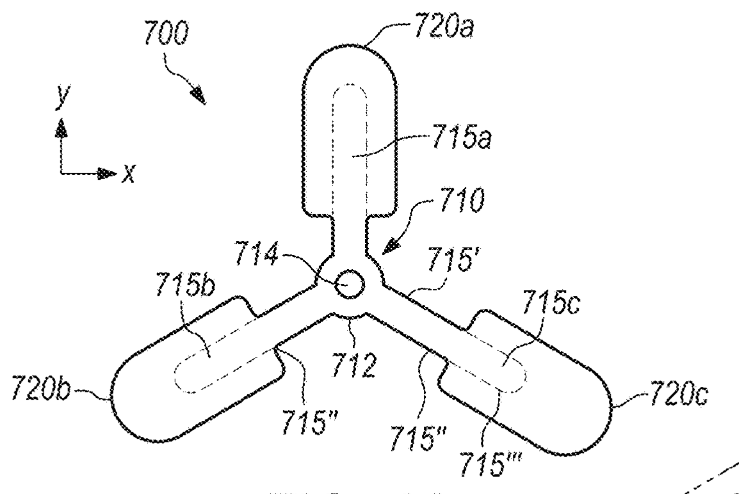
FIGS. 4A-B are elevated end views and FIG. 4C is a perspective side view of the implant distal protection.
Figure 4B:
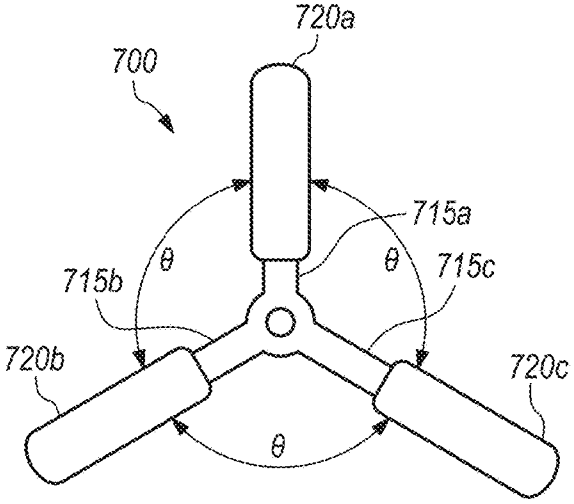
Figure 4C:
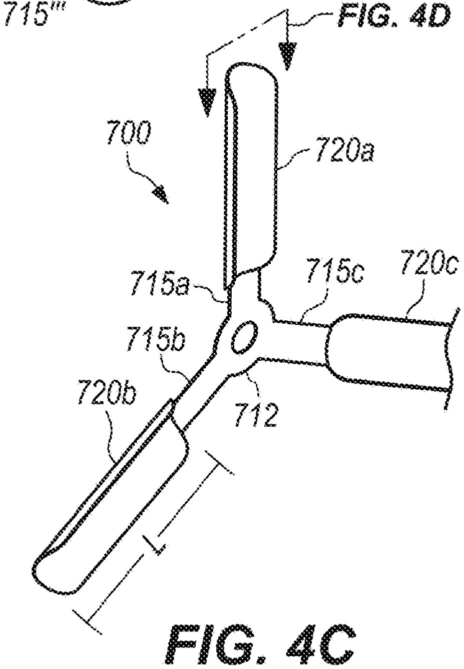
Figure 4D:
FIG. 4D is cross-sectional view of a petal like member and FIG. 4E is a perspective side view of the implant distal protection, according to embodiments of the disclosed inventions.
Figure 4E:
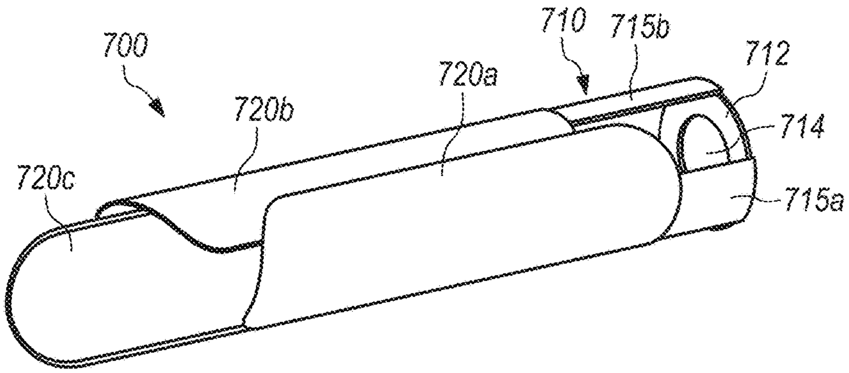

FIGS. 4A-4E illustrate the implant distal protection 700 of the delivery wire assembly 300, according to one embodiment of the disclosed inventions. FIGS. 4A-B are elevated end views and FIG. 4C is a perspective side view of the implant distal protection 700 in an unconstrained deployment configuration; FIG. 4D is cross-sectional view of a petal like member and FIG. 4E is a perspective side view of the implant distal protection 700 in a radially constrained delivery configuration. The implant distal protection 700 is composed of biocompatible material, such as TFN, ePTFE, polymers, Nitinol or the like. In one embodiment, the implant distal protection 700 comprises a reinforcement member 710 having three elongated arms, ribs or stems 715*a*-715*c* extending from a central portion 712. The central portion 712 includes an opening 714 configured to receive or be disposed around the core wire 350 of the implant delivery wire assembly 300. The central portion 712 and the opening 714 may have respective circular configurations, as shown in FIGS. 4A-4E, or any other suitable configuration (not shown). Stems 715*a*-715*c* extend from and are disposed around the central portion 712 of the implant distal protection 700. Each stem 715*a*-715*c* has a respective proximal section 715', a middle section 715" and a distal section 715'". The respective proximal sections 715' of the stems 715*a*-715*c* are coupled to the central portion 712 of the implant distal protection 700. The central portion 712 and the stems 715*a*-715*c* are composed of Nitinol or any other suitable superelastic material.

In some embodiments, as shown in FIG. 4A-B, the stems 715*a*-715*c* are symmetrically disposed with respect to a y-axis, around the central portion 712, such as, stem 715*a* is at angle θ, approximately 120° apart from stem 715*b*, stem 715*b* is also at angle θ, approximately 120° apart from stem 715*c*, and stem 715*c* is at angle θ, approximately 120° apart from stem 715*c*. It should be appreciated that stems 715*a*-715*c* may be disposed in a non-symmetrical configuration around the central portion 712, at any suitable angle θ separation (not shown).

In the embodiments of FIGS. 4A-4E, the implant distal protection 700 further comprises three petal-like members (or "petals") 720*a*-720*c* disposed over each of the respective stems 715*a*-715*c*. The petal-like members 720*a*-720*c* are composed of substantially uniform layers of ePTFE, each having a thickness of approximately between 0.0152 millimeters (0.0006 inches) to 0.030 millimeters (0.0012 inches). The petals 720*a*-720*c* are composed of biocompatible material, such as TFN, ePTFE, polymers, combination thereof or the like. For example, commercially-available Polyimide (PI) film with FEP coating could be used external or internal to the ePTFE material for the petal-like members 720*a*-720*c*. Additionally or alternatively, FEP-coated PI film may be incorporated between layers of ePTFE during the sintering process of manufacturing of the petal-like members 720*a*-720*c*.

As shown in FIGS. 4A-B, each of the petals 720*a*-720*c* may be disposed on or cover approximately between 40% to 90% of each of their respective stems 715*a*-715*c*. As better appreciated in the embodiment of FIG. 4A depicting the contour of the stems 715*a*-715*c* within the petals 720*a*-720*c*, the petal 720*a* is disposed on or cover between approximately 80% to 90% of the stem 715*a*, the petal 720*b* is disposed on or cover between approximately 50% to 60% of the stem 715*b*, and the petal 720*c* is disposed on or cover between approximately 40% to 30% of the stem 715*c*. Such as, the proximal sections 715' of stems 715*a*-715*c* are not covered by the petals 720*a*-720*c*, a small part of the middle section 715" of 715*b* is not covered by petal 720*b* and a larger part of the of the middle section 715" of 715*c* is not covered by petal 720*c*.

Although in the implant distal protection 700 of FIGS. 4A-4E the petals 720*a*-720*c* have the same length, petal 720*c* extends further distally than petals 720*a*-720*b*, and petal 720*b* extends further distally than petal 720*a*. The petals 720*a*-720*b* extend "distally" with respect to the central portion 712 of the implant distal protection 700, however, as it will be described in further detail below, the petals 720*a*-720*b* will be proximally directed, when the implant distal protection 700 is not constrained within the delivery catheter 120.

It should be appreciated that the petals 720*a*-720*c* may include different lengths and be disposed around the same sections over their respective stems 715*a*-715*c* to create a similar implant distal protection having different distally extending petals-like members. The different distally extending petals 720*a*-720*c* of FIGS. 4A-4E are configured to provide implant coverage with minimal material for better flushing during delivery of the implant 200. Additionally, the different distally extending petals 720*a*-720*c* of the implant distal protection 700 are configured to allow sequential deployment each of the petals 720*a*-720*c* as they exit the delivery catheter 120 (e.g., via the delivery catheter 120 being withdrawn proximally relative to the core wire 350, or the core wire 350 being pushed distally relative to the delivery catheter 120, or some of each, thereby exposing the implant distal protection 700 out the distal end opening 452 of the delivery catheter 120) avoiding or minimizing the risk of entanglement of the petals 720*a*-720*c* and/or avoiding or minimizing potential failure of the implant distal protection 700 (e.g., failure to radially expand). The sequential radial expansion of the petals 720*a*-720*c* (e.g., no longer radially constrained by the delivery catheter 120) would be in the following order of: i) first, petal 720*a*, then ii) the petal 720*b* and finally, iii) petal 720*c*, as it will be described in further detailed below.

As better appreciated in FIGS. 4C-4D depicting a perspective side view and a cross-section of the implant distal protection 700, the petals 720*a*-720*c* of FIGS. 4A-E have an arcuate configuration along the length L of the petals. For example, FIG. 4D depicts a cross-sectional view of the petal 720*b* having an arcuate, annular strip, concave configuration, as also appreciated in FIG. 4E. FIG. 4E depicts a perspective side view of the implant distal protection 700 in a radially constrained delivery configuration, additionally showing the different distally extending petals 720*a*-720*c* with respect to the central portion 712, having petal 720*c* extending further distally that any of the other petals 720*a*-720*b*, and petal 720*b* extends further distally that the petal 720*a*.

Figure 5A:
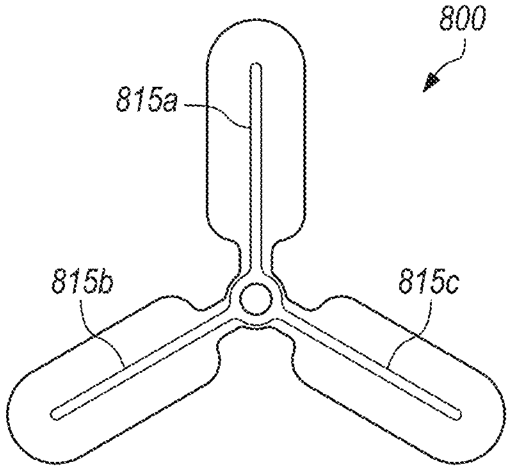
FIGS. 5A-B are elevated end and partial views of an implant distal protection.
Figure 5B:
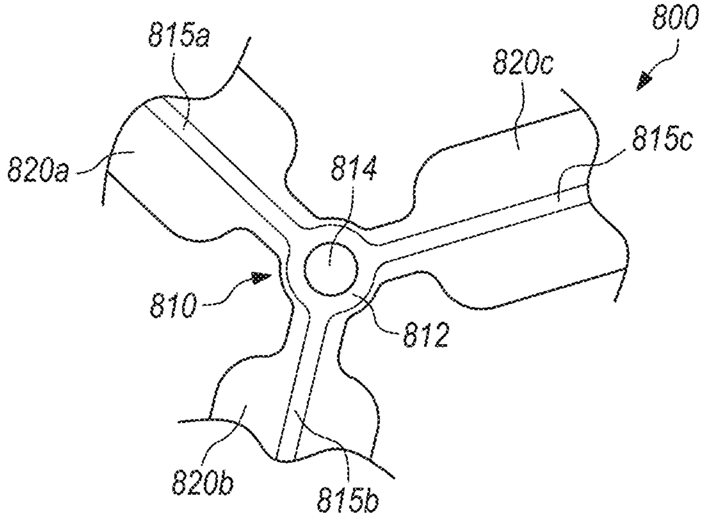
Figure 5C:
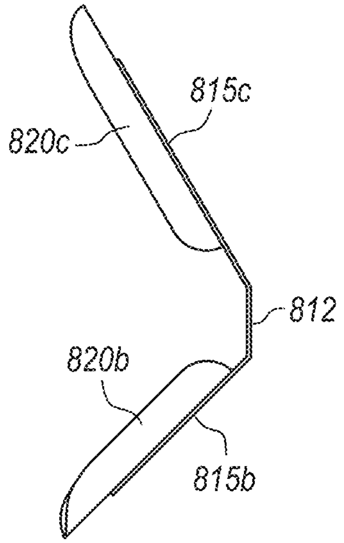
FIG. 5C is a perspective side view of the implant distal protection 800, according to alternative embodiments of the disclosed inventions.

FIGS. 5A-5C illustrate an alternative implant distal protection 800 of the delivery wire assembly 300, according to further embodiments of the disclosed inventions. FIGS. 5A-B are elevated end and partial views of the implant distal protection 800 in an unconstrained deployment configuration; and FIG. 5C is a perspective side view of the implant distal protection 800 in a radially constrained delivery configuration. Similar to the implant distal protection 700 of FIGS. 4A-B, the implant distal protection 800 comprises a reinforcement member 810 having three elongated arms, ribs or stems 815*a*-815*c* extending from a central portion 812. The central portion 812 includes an opening 814 configured to receive or be disposed around the core wire 350 of the implant delivery wire assembly 300.

Further, the implant distal protection 800 of FIGS. 5A-5C is similar to the implant distal protection 700 of FIGS. 4A-B, except that the implant distal protection 800 FIGS. 5A-5C have petals 820*a*-820*c* that are composed of an unitary thin, substantially uniform layer of ePTFE, or other suitable material. As better shown in FIG. 5B, the petals 820*a*-820*c* meet at a central portion 812 that is configured to be coupled to the core wire 350. As shown in FIGS. 5B-5C, the petals 820*a*-820*c* extend generally radially outward from the central portion 812, and proximally directed, when the implant distal protection 800 is not constrained within the delivery catheter 120. Although the petals 820*a*-820*c* are composed of a substantially uniform layer of ePTFE, or other suitable material, the implant distal protection 800 of FIGS. 5A-5C also have different distally extending petals 820*a*-820*c* with respect to the central portion 812, having petal 820*c* extending further distally than any of the other petals, in particular petal 820*b*, as better appreciated in FIG. 5C.

Figure 6:
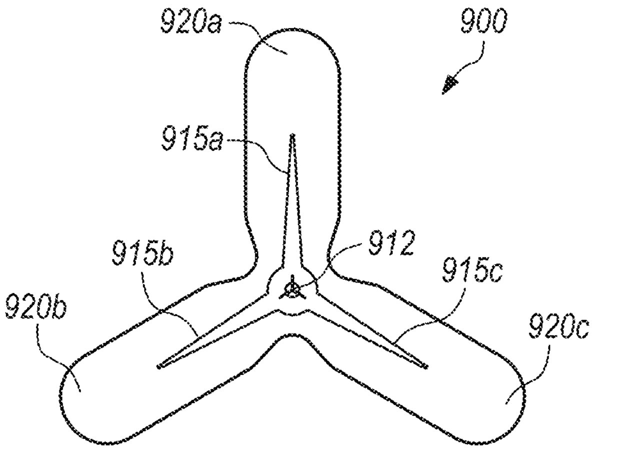
FIG. 6 is an alternative implant distal protection, similar to that of FIGS. 5A-5C.

FIG. 6 illustrates another alternative implant distal protection 900 of the delivery wire assembly 300, according to other embodiments of the disclosed inventions. The implant distal protection 900 includes three elongated arms, ribs or stems 915*a*-915*c* extending from a central portion 912. The implant distal protection 900 of FIG. 6 is similar to that of FIGS. 5A-5C, except that more material of the unitary thin, substantially uniform layer of ePTFE forming petals 920*a*-920*c* is disposed around the central portion 912.

Figure 7A:
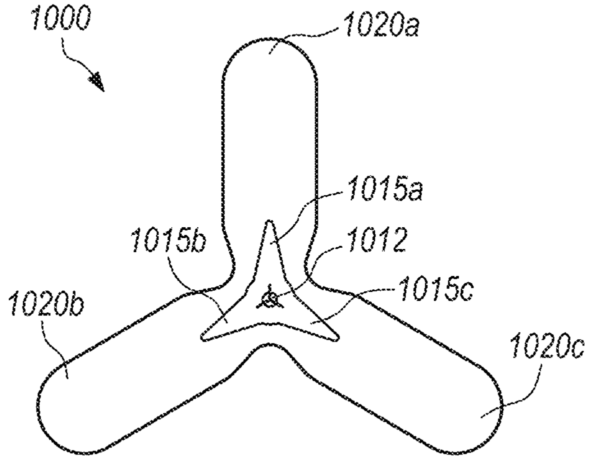
FIGS. 7A-7B are another alternative implant distal protection, according to other embodiments of the disclosed inventions.
Figure 7B:
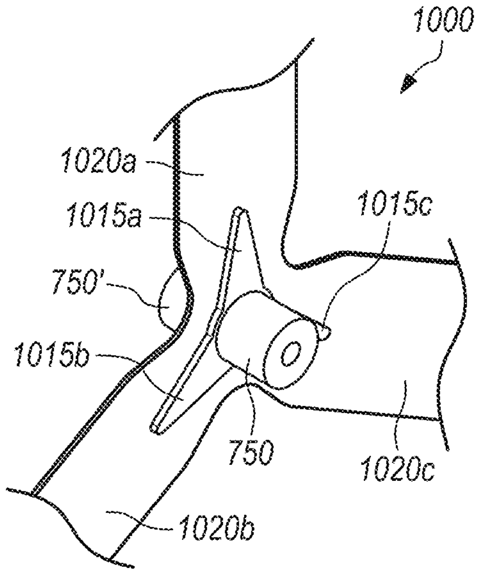

FIGS. 7A-7B illustrate yet another alternative implant distal protection 1000 of the delivery wire assembly 300, according to other embodiments of the disclosed inventions. The implant distal protection 1000 of FIGS. 7A-7B has three petals 1020*a*-1020*c* disposed around the central portion 1012. The implant distal protection 1000 of FIGS. 7A-7B are similar to that of FIG. 6, except that the three elongated arms, ribs or stems 1015*a*-1015*c* extending from a central portion 1012 are shorter than the stems 915*a*-915*c* of FIG. 6. Additionally, FIG. 7B illustrate the distal locking member 750 (also shown in FIGS. 3A-3B) and the proximal locking member 750' coupled to the implant distal protection 1000. Further in the implant distal protection 1000 (as better appreciated in FIG. 7B), the stems 1015*a*-1015*c* are disposed over or side-by-side to petals 1020*a*-1020*c*.

Figure 8:
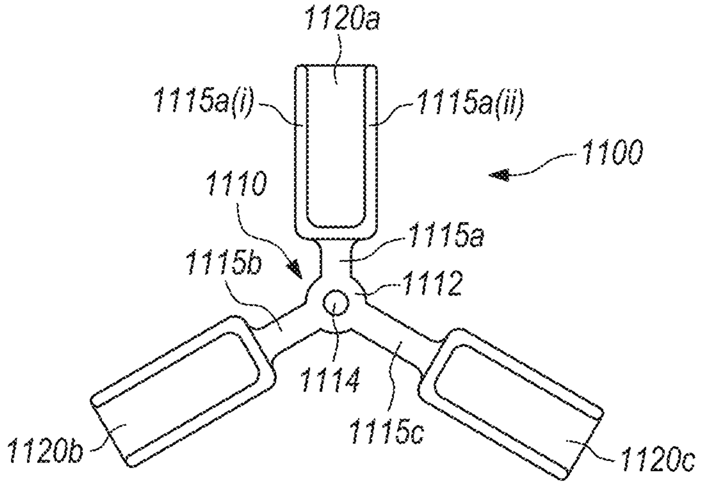
FIG. 8 is yet another alternative implant distal protection, according to further embodiments of the disclosed inventions.

FIG. 8 illustrates an alternative implant distal protection 1100 of the delivery wire assembly 300, according to other embodiments of the disclosed inventions. Similar to the implant distal protection 700 of FIGS. 4A-E, FIG. 9 comprises different distally extending petals 1120*a*-1120*c* with respect to a central portion 1112, having petal 1120*c* extending further distally than any of the other petals 1120*a*-1120*b*, and petal 1120*b* extends further distally than the petal 1120*a*. The implant distal protection 1100 further comprises a reinforcement member 1110 having three elongated bifurcated arms, ribs or stems 1115*a*-1015*c* extending from the central portion 1112. The central portion 1112 includes an opening 1114 configured to receive or be disposed around the core wire 350 of the implant delivery wire assembly 300. The bifurcated stems 1115*a*-1115*c* extend from and are disposed around the central portion 1112 of the implant distal protection 1100. Each stem 1115*a*-1115*c* bifurcates into two branches having respective petals 1120*a*-1120*c* disposed between each of their respective branches, as shown in FIG. 8. For example, stem 1115*a* bifurcates into a first branch 1115*a* (i) and a second branch 1115*a* (ii) forming a "U" like configuration and having petal 1120*a* disposed between branches 1115*a* (i) and 1115*a* (ii). The bifurcated stems 1115*a*-1115*c* of FIG. 8 are configured to provide additional structural support to the petals 1120*a*-1120*c* allowing the petals to be proximally directed, when the implant distal protection 1100 is not constrained within the delivery catheter 120.

It should be appreciated that the petals of FIGS. 5A-8 have an arcuate, annular strip, concave cross-sectional configuration, as shown in FIG. 4D. Other suitable cross-sectional configuration of the petals of FIGS. 5A-8 could be considered. In other embodiments (not shown), the implant distal protection 700 may include more or less than three stems and/or petals configured to deployed sequentially, as described in further detail below.

FIGS. 9A-D illustrate the front loading of the delivery wire assembly 300 into the delivery catheter 120, according to one embodiment of the disclosed inventions. The implant distal protection 700 of FIGS. 4A-E is shown in FIGS. 9A-D as an exemplary distal protection used to load the delivery wire assembly 300, including implant 200 into the delivery catheter 120. It should be appreciated that any of the implant distal protections disclosed in the alternative embodiments of FIGS. 5A-8 may be used to load the delivery wire assembly 300, including implant 200 and into the delivery catheter 120.

Figure 9A:
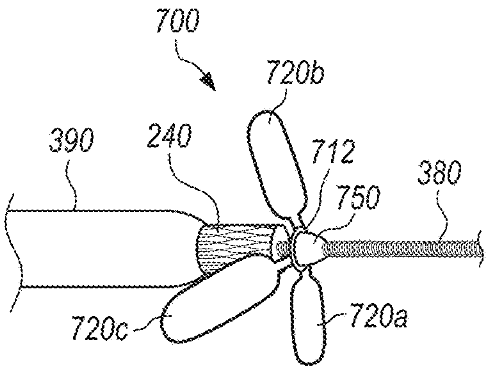
FIGS. 9A-D are cut-away, side and perspective views of the implant distal protection of FIGS. 4A-4E depicted as the delivery wire assembly is loaded into the delivery catheter 120, according to embodiments of the disclosed inventions.

FIG. 9A depicts the distal end portion of the delivery wire assembly 300, including the implant distal protection 700 and implant 200, just prior to being loaded into the delivery catheter 120, wherein the petals 720*a*-720*c* of the implant distal protection 700 are shown extending generally proximally in a radially unconstrained configuration. As described above, the implant distal protection 700 comprises different extending petals 720*a*-720*c* (e.g., distally with respect to the central portion 712, FIGS. 4A-4E), where the difference in the extension of the petals 720*a*-720*c* of the implant distal protection 700 are shown as proximally directed with respect to the implant 200. As such, petal 720*c* extending further proximately towards the implant 200 that any of the other petals 720*b*-720*a*, and petal 720*b* extends further proximately than the petal 720*a*.

The implant 200 is coaxially disposed around the core wire 350 (not shown), and held in the radially constrained delivery configuration by a tubular loading member 390, with the distal end portion 240 of the implant 200 is partially exposed out a distal end opening of the loading member 390.

Figure 9B:
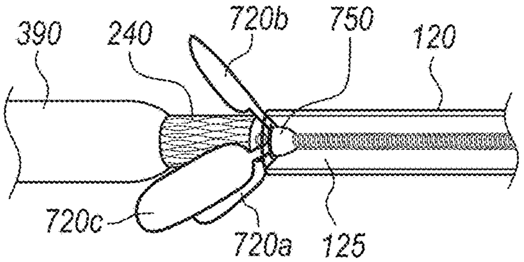
Figure 9C:
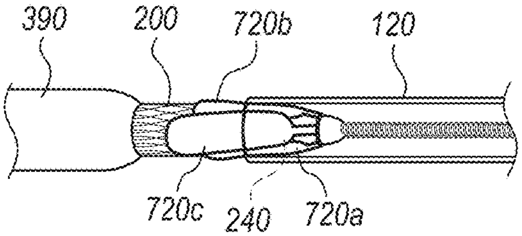

The distal end portion of the delivery wire assembly 300, including the implant distal protection 700 and the compressed implant 200, is either advanced into the delivery catheter 120, or the delivery catheter 120 is advanced over the distal portion of the delivery wire assembly 300, or some of each, thereby radially compressing the petals 720*a*-720*c* of the implant distal protection 700 over and onto the distal portion 240 of the implant 200, as shown in FIGS. 9B-C. Additionally or alternatively, the radial compression of the 720*a*-720*c* of the implant distal protection 700 over and onto the distal portion 240 of the implant 200, may be assisted by orderly compressing the petals, such as, first, compressing petal 720*c*, then, compressing petal 720*b*, and lastly compressing petal 720*a*. The radially compressed petals 720*a*-720*c* are disposed on and/or partially covering the distal portion 240 of the implant 200. In some embodiments, the stems 715*a*-715*c* are not disposed on and do not cover the distal portion 240 of the implant 200, as shown in FIGS. 9A-9B and FIGS. 10A-10D.

Figure 9D:
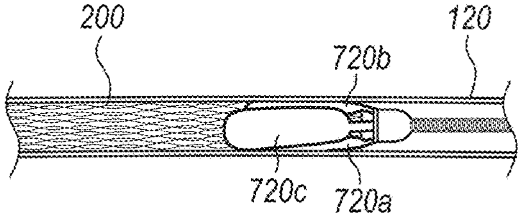

Once the delivery catheter 120 is disposed over the respective implant distal protection 700 and loading member 390, the loading member 390 is withdrawn, while the implant 200 remains in the compressed delivery configuration within the lumen 125 of the delivery catheter 120, and the petals 720*a*-720*c* of the implant distal protection 700 remain compressed onto, and at least partially covering the distal portion 240 of the implant 200 (FIG. 9D).

Although the disclosed inventions are not so limited, the illustrated "three-petal" configuration (e.g., stems and petals) of the implant distal protections 700-1100 are configured to minimize the amount of material covering the distal end of the distal portion 240 of the implant 200, thereby reducing and minimizing resistive or frictional forces imparted by the implant on the inner wall of the delivery catheter 120 as the implant 200 is pushed through the lumen 125. In particular, the inventor(s) of the disclosed inventions have found that, by employing the depicted configuration of the implant distal protections 700-1100, the coefficient of friction between the implant 200 and the inner wall of the delivery catheter 120 ranges from approximately 0.01 to approximately 0.04 when there is relative motion between the core wire 350 and the delivery catheter 120.

In various embodiments, the implant distal protections 700-1100 are sized and configured to cover differing amounts of the distal end portion 240 of the implant 200 when a distal portion of the delivery wire assembly 300 including the implant 200 and implant distal protections 700-1100 are constrained within the delivery catheter lumen 125. By way of non-limiting examples, in one embodiment, the implant distal protections 700-1100 are sized and configured to cover as much as about twenty percent of a total length of the implant 200 when a distal portion of the delivery wire assembly 300 including the implant 200 and implant distal protections 700-1100 are constrained within the delivery catheter lumen 125. In another embodiment, the implant distal protections 700-1100 are sized and configured to cover between about ten percent and about twenty percent of a total length of the implant 200 when a distal portion of the delivery wire assembly 300 including the implant 200 and the implant distal protections 700-1100 are constrained within the delivery catheter lumen 125. In still another embodiment, the implant distal protections 700-1100 are sized and configured to cover between about five percent and about ten percent of a total length of the implant 200 when a distal portion of the delivery wire assembly 300 including the implant 200 and implant distal protections 700-1100 are constrained within the delivery catheter lumen 125. In yet another embodiment, the implant distal protections 700-1100 are sized and configured to cover about five percent or less of a total length of the implant 200 when a distal portion of the delivery wire assembly 300 including the implant 200 and implant distal protections 700-1100 are constrained within the delivery catheter lumen 125.

FIGS. 10A-H illustrate the implant distal protection 700 for delivery and deployment of the implant 200 to/at a targeted site in a vasculature (not shown). The implant distal protection 700 of FIGS. 4A-E is shown in FIGS. 10A-E as an exemplary distal protection used for the delivery and deployment of the implant 200. It should be appreciated that any of the implant distal protections disclosed in the alternative embodiments of FIGS. 5A-8 may be used for the delivery and deployment of the implant 200 to/at a targeted site.

Figure 10A:
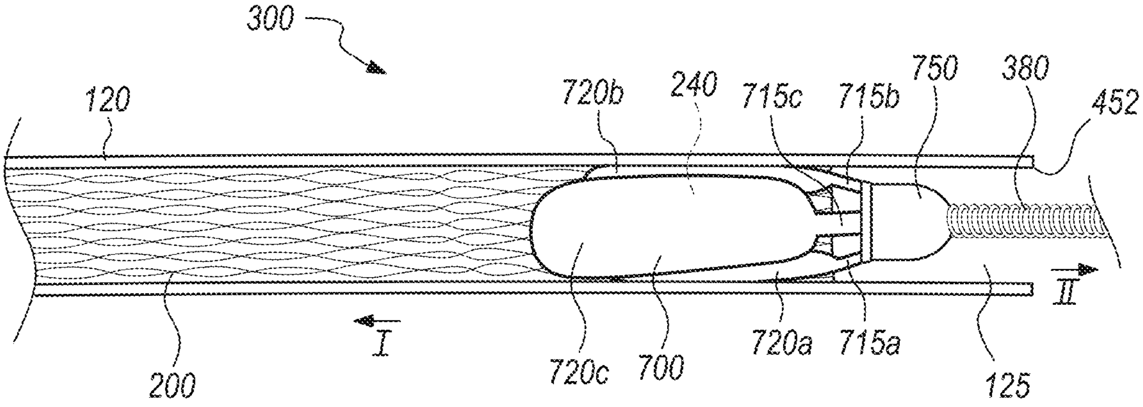
FIGS. 10A-H are side and perspective views of the implant distal protection of FIGS. 4A-4E depicted during delivery and deployment of an implant at a targeted site in a vasculature using the implant delivery system of FIGS. 1-3.
Figure 10B:
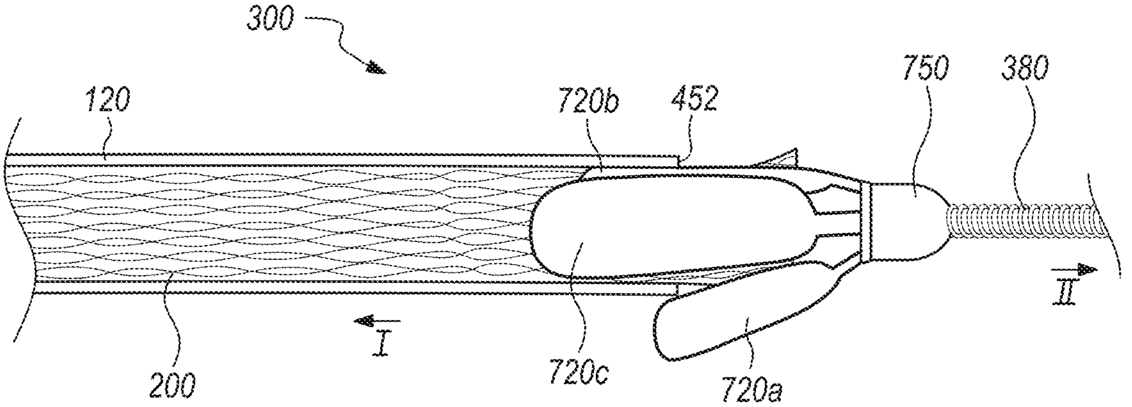
Figure 10C:
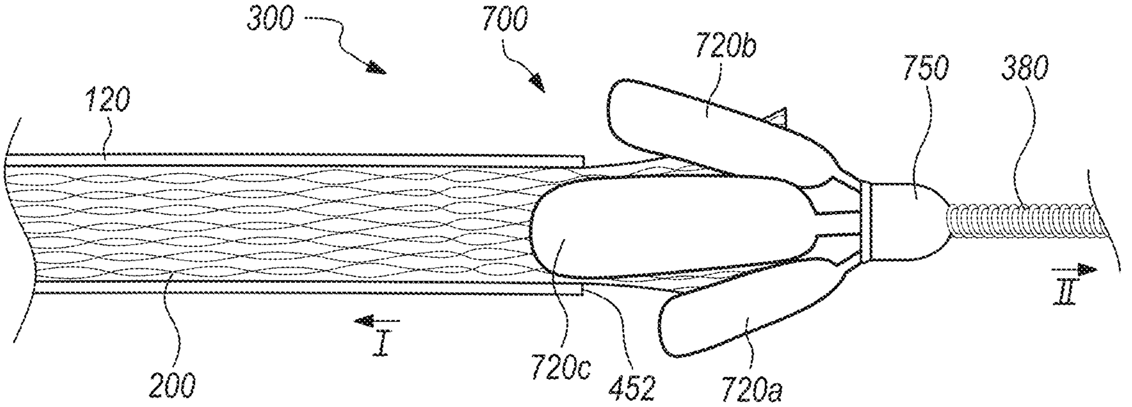
Figure 10D:
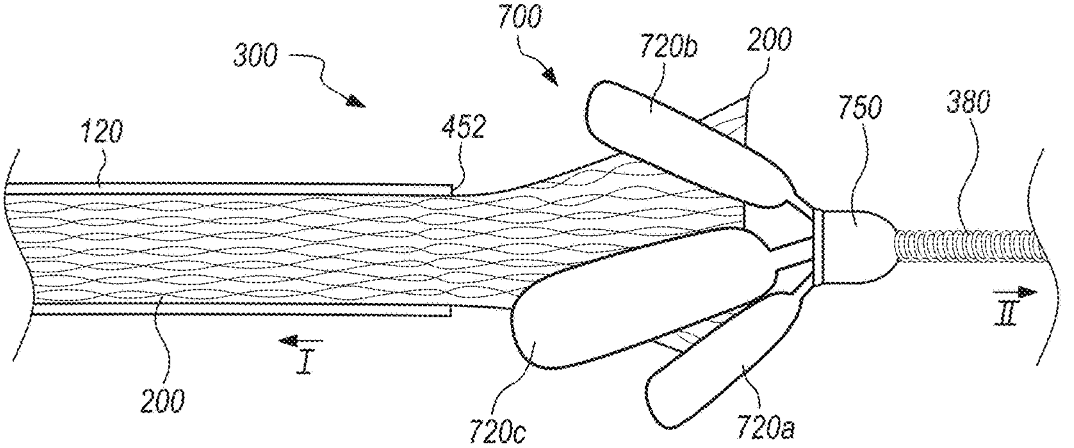
Figure 10E:
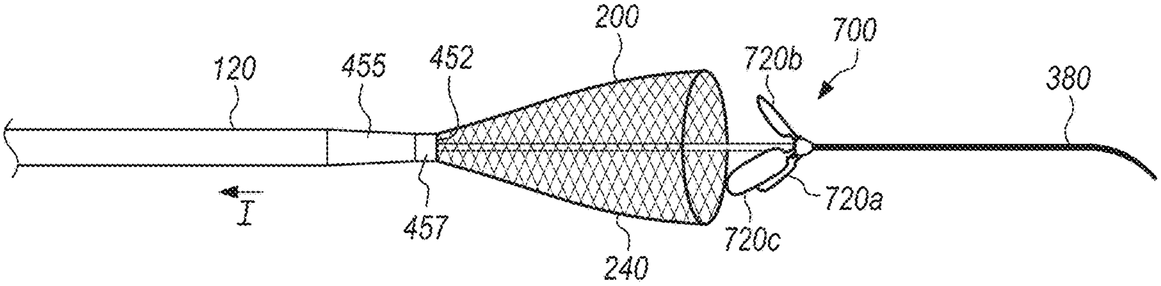
Figure 10F:
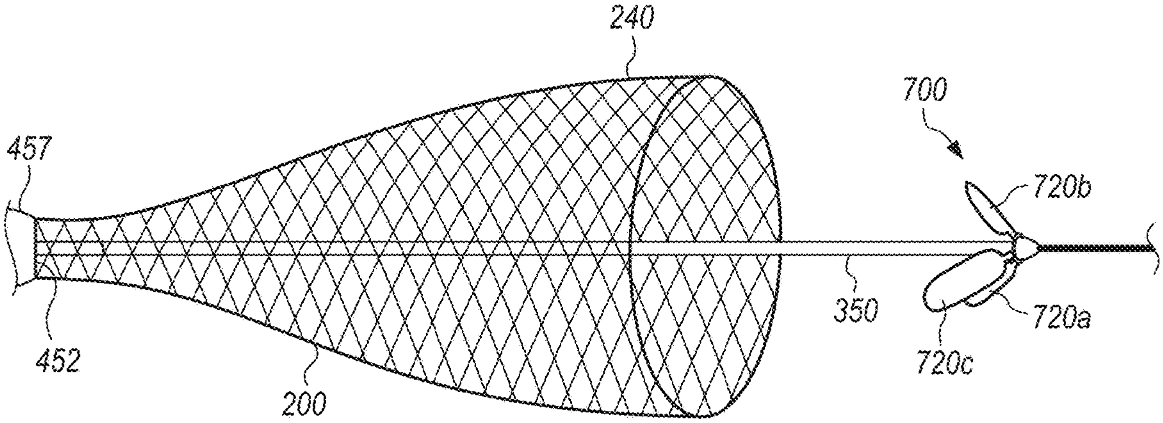

FIG. 10A depicts a distal end portion of the delivery wire assembly 300 as the core wire 350 (not seen in FIG. 10A) is pushed through the delivery catheter lumen 125. The implant 200 and distal implant protection 700 are shown in the compressed delivery configuration, constrained within the delivery catheter lumen 125, with the petals 720*a*-720*c* of implant distal protection 700 covering and protecting the distal portion 240 of the implant 200.

Once the distal end portion of the delivery assembly 300 is located proximate to the targeted implantation site, the delivery catheter 120 is withdrawn proximally relative to the core wire 350 (shown by arrows I), or the core wire 350 is pushed distally relative to the delivery catheter 120 (shown by arrows II), or some of each, thereby exposing the implant distal protection 700 and the implant 200 out the distal end opening 452 of the delivery catheter 120, allowing the no-longer radially constrained implant 200 to self-expand radially, starting at the distal end portion 240, to the expanded configuration, as shown in FIGS. 10B-10E.

As the petals 720*a*-720*c* of the implant distal protection 700 have different extending lengths (e.g., petal 720*a* is shorter than either petals 720*b*-720*c*, petal 720*b* is shorter than petal 720*c* but longer than petal 720*c*, and petal 720*c* is longer than either petals 720*a*-720*b*), the implant distal protection 700 is configured to allow sequential deployment each of the petals 720*a*-720*c* as they exit out of the distal end opening 452 of the delivery catheter 120 avoiding or minimizing the risk of entanglement of the petals 720*a*-720*c* and/or avoiding or minimizing potential failure of the implant distal protection 700 (e.g., failure to radial expand). The sequential exit out of the delivery catheter 120 and radial expansion of the petals 720*a*-720*c* would be in the following order of: i) first, petal 720*a*, as the shortest of the petals (FIG. 10B), then ii) the petal 720*b* as the middle size (FIG. 10C), and finally, iii) petal 720*c* as the longest of the petals (FIG. 10D), to exit out of the distal end opening 452 of the delivery catheter 120. Notably, the petals 720*a*-720*c* remain generally extending in the proximal direction (i.e., in the "delivery configuration") as the distal end portion 240 of the implant 200 assumes the expanded configuration and is no longer covered by the implant distal protection 700, as shown in FIGS. 10D-10H.

Further, the implant distal protection 700 respective stems 715*a*-715*c* are composed of Nitinol or any suitable super-elastic material, such that the stems 715*a*-715*c* are configured assist and further allow radial expansion of their respective petals 720*a*-720*c* with elastic energy during deployment of the implant 200 and release of the distal end portion 240 of the implant, yet the petals 720*a*-720*c* remain extending in the proximal direction (e.g., facing toward the implant 200) in the delivery configuration (FIGS. 10A-10H). This feature further facilitates and allows recapture of the implant distal protection 700 during pullback into the delivery catheter 120 after the implant 200 is deployed to/at a targeted site (not shown).

The implant distal protection 700 is configured to exert negligible or otherwise insignificant forces over the distal portion 240 of the implant 200 as the implant 200 expands. In some embodiments, the implant distal protection 700 may outwardly radially expand when no longer radially constrained by the delivery catheter 120. In the described embodiments, when the implant distal protection 700 retains the delivery configuration or outwardly expands when no longer constrained by the delivery catheter 120, the petals 720*a*-720*c* are configured to extend and/or face in a proximal direction, (i.e., oriented towards the delivery system or implant, the individual petals 720*a*-720*c* preferably do not evert as the implant 200 expands).

Figure 10G:
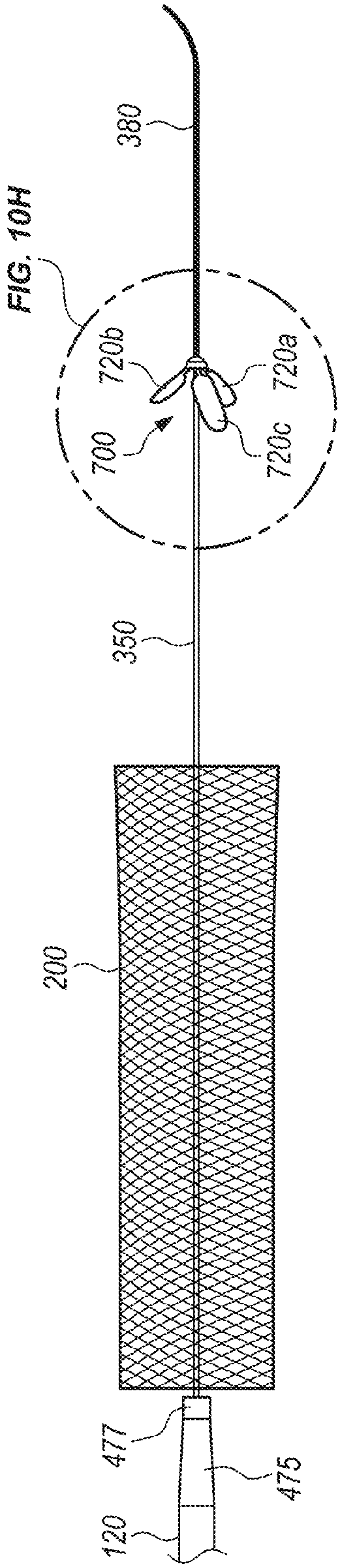
Figure 10H:
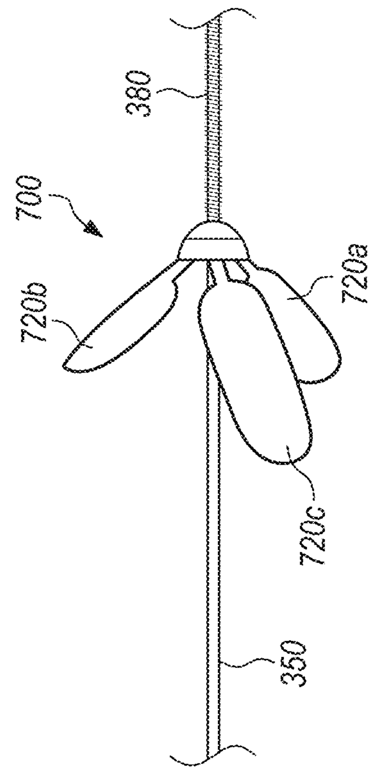

After deployment of the implant 200 at the targeted site, the delivery wire assembly 300 is withdrawn back into the delivery catheter (not shown), and the delivery system 100 is withdrawn from the body, leaving the expanded implant 200 implanted at the targeted site. Notably, the core wire 350 and distal implant protection 700 are pulled through the lumen 260 of the implant 200 and back into the delivery catheter lumen 125 without interfering with the deployed expanded implant 200, due to the implant distal protection 700 "proximal facing" configuration and its relatively small size with respect to the expanded implant 200, as shown in FIG. 10G-10H. FIG. 10H is an enlarged view of the section shown in FIG. 10G, to better illustrate that the implant distal protection 700 substantially retains its delivery configuration even when the delivery catheter 120 is no longer constraining the implant distal protection 700.

The implant distal protection 700 may be fixedly attached to the core wire 350 by the locking members 750, so that the implant distal protection does not rotate relative to the core wire 350. Alternatively, the implant distal protection 700 may by rotatable relative to the core wire 350 and locking members 750. The rotatable implant distal protection 700 is configured to allow torque transmission to the distal end of the core wire 350 (e.g., atraumatic distal tip portion 380), which further allows vessel selection and facilitates navigation of the delivery wire assembly 300 to the targeted implantation site. When the implant distal protection 700 rotates with respect to the core wire 350, any externally induced (e.g., by patient's anatomy, user, clinician) relative torsion between the delivery catheter 120 and the core wire 350 is avoided or substantially minimized, preventing accumulation of torsional energy, detrimental to the deployment of the implant 200. As such, the rotatable implant distal protection 700 is configured to prevent accumulation of torsional energy in the delivery wire assembly 300 and the implant 200, when assembly 300 and implant 200 are radially constrained within the lumen 125 of the delivery catheter 120. Further, the rotatable implant distal protection 700 is configured to allow the petals 720*a*-720*c* to be coupled (e.g., maintain contact) to the implant 200 in the delivery configuration, when the core wire 350 is subjected to torsion.

It should be appreciated that any of the features disclosed for the implant distal protection 700, particularly in FIGS. 9A-10H, are also disclosed for the alternative embodiments of FIGS. 5A-8 except where they expressly differed, as described above.

Although particular embodiments have been shown and described herein, it will be understood by those skilled in the art that they are not intended to limit the disclosed inventions, and it will be obvious to those skilled in the art that various changes, permutations, and modifications may be made (e.g., the dimensions of various parts, combinations of parts) without departing from the scope of the disclosed inventions, which is to be defined only by the following claims and their equivalents. The specification and drawings are, accordingly, to be regarded in an illustrative rather than restrictive sense, and the embodiments depicted and described herein are intended to cover alternatives, modifications, and equivalents of thereof, which may be included within the scope of the appended claims.

The invention claimed is:

1. A delivery system for deploying an implant at a target site within a mammalian vasculature, the implant having a compressed delivery configuration and an expanded deployed configuration, the delivery system comprising:

a delivery catheter having a lumen;

an elongate delivery wire assembly at least partially disposed within the delivery catheter lumen, the delivery wire assembly being translatable relative to the delivery catheter and having an implant loading region configured for seating the implant when a distal portion of the delivery wire assembly including the implant is constrained within the delivery catheter lumen and the implant is in the compressed delivery configuration; and an implant distal protection feature comprising a central portion coupled to the delivery wire assembly distally of the implant loading region, and a peripheral portion comprising reinforcement member having a plurality of circumferentially spaced elongated stems that extend proximally from the central portion, and a plurality of petal-like members respectively disposed on the plurality of circumferentially spaced elongated stems, wherein the plurality of petal-like members at least partially covers a distal end portion of the implant when the implant and implant distal protection feature are constrained within the delivery catheter lumen, wherein the reinforcement member is configured to facilitate radial expansion of the plurality of petal-like members with elastic energy when the implant is released from the delivery catheter lumen and assumes the expanded deployed configuration.

2. The delivery system of claim 1, wherein the respective petal-like members are configured to collective cover the elongated stems when the implant and implant distal protection feature are constrained within the delivery catheter.

3. The delivery system of claim 1, wherein the respective stems and petal-like members of the implant distal protection feature are configured to expand from a compressed delivery configuration to an expanded deployed configuration in a sequential order in which the first petal-like member expands first, the second petal-like member expands after the first petal-like member, and the third petal-like member expands after the second petal-like member.

4. The delivery system of claim 1, wherein the stems and petal-like members are substantially evenly circumferentially spaced around the delivery wire assembly.

5. The delivery system of claim 1, wherein the petal-like members comprise an arcuate, annular strip, or concave configuration.

6. The delivery system of claim 1, wherein the central portion of the implant distal protection feature is fixedly attached to the delivery wire assembly.

7. The delivery system of claim 1, wherein the central portion of the implant distal protection feature is rotatably coupled to the delivery wire assembly.

8. The delivery system of claim 1, wherein the respective stems and petal-like portions of the implant distal protection feature are configured to not evert to a distally facing direction as the implant expands from the compressed delivery configuration to the expanded deployed configuration.

9. The delivery system of claim 1, wherein the peripheral portion of the distal protection feature comprises more than three stems with petal-like members.

10. The delivery system of claim 9, wherein each petal-like member covers a different percentage of a length of the corresponding stem when the implant and implant distal protection feature are constrained within the delivery catheter.

11. The delivery system of claim 1, wherein the reinforcement member and the petal-like members are composed of different materials.

12. The delivery system of claim 11, wherein the petal-like members include a first petal-like member disposed on or covering between about eighty percent to about ninety percent of a total length of the respective elongated stem, a second petal-like member disposed on or covering between about sixty percent to about fifty percent of the total length of the respective elongated stem, and a third petal-like member disposed on or covering between about forty percent to about thirty percent of the total length of the respective elongated stem.

13. The delivery system of claim 11, wherein the petal-like members are composed of a polymeric material, and the reinforcement member is composed of a metallic material.

14. The delivery system of claim 13, wherein the respective stems and petal-like members of the implant distal protection feature are configured to expand from a compressed delivery configuration to an expanded deployed configuration in a sequential order in which the first petal-like member expands first, the second petal-like member expands after the first petal-like member, and the third petal-like member expands after the second petal-like member.

15. The delivery system of claim 13, wherein the polymeric material is ePTFE, and the metallic material is Nitinol.

16. The delivery system of claim 1, wherein the petal-like members extend proximally from the central portion of the implant distal protection feature.

17. The delivery system of claim 1, wherein each of the stems is bifurcated and has two branches, wherein each of the petal-like members is disposed between the two branches of a respective one of the stems.

18. The delivery system of claim 1, wherein at least two of the petal-like members have different lengths relative to each other.

19. A delivery system for deploying an implant at a target site within a mammalian vasculature, the implant having a compressed delivery configuration and an expanded deployed configuration, the delivery system comprising:

a delivery catheter having a lumen;

an elongate delivery wire assembly at least partially disposed within the delivery catheter lumen, the delivery wire assembly being translatable relative to the delivery catheter and having an implant loading region configured for seating the implant when a distal portion of the delivery wire assembly including the implant is constrained within the delivery catheter lumen and the implant is in the compressed delivery configuration; and an implant distal protection feature comprising a central portion coupled to the delivery wire assembly distally of the implant loading region, and a peripheral portion comprising a plurality of circumferentially spaced elongated stems with petal-like members that extend proximally from the central portion and collectively cover the elongated stems and at least partially cover a distal end portion of the implant when the implant and implant distal protection feature are constrained within the delivery catheter lumen, wherein the respective petal-like members are configured to collective cover the elongated stems when the implant and implant distal protection feature are constrained within the delivery catheter, and wherein the peripheral portion is configured to remain extending proximally from the central portion when the implant is released from the delivery catheter lumen and assumes the expanded deployed configuration.

20. The delivery system of claim 19, wherein the petal-like members include a first petal-like member disposed on or covering between about eighty percent to about ninety percent of a total length of the respective elongated stem, a second petal-like member disposed on or covering between about sixty percent to about fifty percent of the total length of the respective elongated stem, and a third petal-like member disposed on or covering between about forty percent to about thirty percent of the total length of the respective elongated stem.

* * * * *